US010449095B2

(12) United States Patent
Morimoto (10) Patent No.: US 10,449,095 B2
(45) Date of Patent: *Oct. 22, 2019

(54) WEARABLE ARTICLE HAVING ELASTIC BELT

(71) Applicant: The Procter & Gamble Company, Cincinnati, OH (US)

(72) Inventor: Koichi Morimoto, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 95 days.

This patent is subject to a terminal disclaimer.

(21) Appl. No.: 15/632,454

(22) Filed: Jun. 26, 2017

(65) Prior Publication Data

US 2017/0290711 A1    Oct. 12, 2017

Related U.S. Application Data

(63) Continuation of application No. PCT/CN2014/094892, filed on Dec. 25, 2014.

(51) Int. Cl.
*A61F 13/15* (2006.01)
*A61F 13/20* (2006.01)
(Continued)

(52) U.S. Cl.
CPC .. *A61F 13/15585* (2013.01); *A61F 13/49001* (2013.01); *A61F 13/4902* (2013.01);
(Continued)

(58) Field of Classification Search
CPC .......... A61F 13/15585; A61F 13/49001; A61F 13/49011; A61F 13/49014;
(Continued)

(56) References Cited

U.S. PATENT DOCUMENTS 8,382,735 B2   2/2013   Torigoshi et al.
8,518,009 B2   8/2013   Saito et al.
(Continued)

FOREIGN PATENT DOCUMENTS

CN    2668093      1/2005
CN    202699434    1/2013
(Continued)

OTHER PUBLICATIONS

International Search Report and Written Opinion, PCT/CN2014/094892, dated May 28, 2015.
(Continued)

*Primary Examiner* — Michele M Kidwell
(74) *Attorney, Agent, or Firm* — Richard L. Alexander (57) ABSTRACT

Disclosed is a wearable article 20 comprising a main body 38 and a ring-like elastic belt 40 comprising a front belt and a back belt each formed by an inner sheet, an outer sheet, and a plurality of elastic bodies sandwiched therebetween and running in the transverse direction substantially parallel to each other, and at least a portion of the elasticity of at least some of the elastic bodies are removed of its elasticity, the transverse width of the elastic body having the longest length removed of its elasticity defined as a maximum elastic cut window; wherein the length of the article along the longitudinal axis is from 300 mm to 440 mm; and the maximum elastic cut window is less than 100 mm.

18 Claims, 7 Drawing Sheets

(51) Int. Cl.
*A61F 13/496* (2006.01)
*A61F 13/49* (2006.01)
*A61F 13/64* (2006.01)
*A61F 13/56* (2006.01)

(52) U.S. Cl.
CPC ...... *A61F 13/496* (2013.01); *A61F 13/49011* (2013.01); *A61F 13/49014* (2013.01); *A61F 13/49017* (2013.01); *A61F 13/64* (2013.01); *A61F 13/5622* (2013.01); *A61F 2013/49025* (2013.01); *A61F 2013/49088* (2013.01)

(58) Field of Classification Search
CPC ............ A61F 13/49017; A61F 13/4902; A61F 13/496; A61F 13/5622; A61F 13/64; A61F 2013/49025; A61F 2013/49088
See application file for complete search history.

(56) References Cited

U.S. PATENT DOCUMENTS

| | | | |
|---|---|---|---|
| 9,011,404 B2 | 4/2015 | Kobayashi et al. | |
| 9,023,007 B2 | 5/2015 | Hashino et al. | |
| 9,592,163 B2 | 3/2017 | Morimoto et al. | |
| 2009/0030392 A1 | 1/2009 | Kanai et al. | |
| 2009/0118689 A1 | 5/2009 | Lawson et al. | |
| 2010/0286646 A1 | 11/2010 | Takino et al. | |
| 2011/0184372 A1* | 7/2011 | Esping Ostlin | A61F 13/49012 604/392 |
| 2013/0138072 A1 | 5/2013 | Morimoto et al. | |
| 2013/0310795 A1 | 11/2013 | Glahn et al. | |
| 2013/0338623 A1 | 12/2013 | Kinoshita | |
| 2016/0184145 A1* | 6/2016 | Morimoto | A61F 13/49011 604/385.29 |
| 2017/0290716 A1* | 10/2017 | Morimoto | A61F 13/49011 |
| 2017/0290721 A1* | 10/2017 | Morimoto | A61F 13/49011 |
| 2018/0200122 A1 | 7/2018 | Maki | |
| 2018/0333311 A1 | 11/2018 | Maki | |
| 2018/0369027 A1 | 12/2018 | Fukasawa | |

FOREIGN PATENT DOCUMENTS

| | | |
|---|---|---|
| CN | 203354775 | 12/2013 |
| CN | 203885725 | 10/2014 |
| JP | 11188060 | 7/1999 |
| JP | 2013013580 | 1/2013 |
| JP | 2013255561 A | 12/2013 |
| JP | 2013255570 A | 12/2013 |
| JP | 2014147506 | 8/2014 |
| JP | 2018064698 A | 4/2018 |
| JP | 2018138272 A | 9/2018 |
| WO | WO-0185080 | 11/2001 |
| WO | 2009119195 | 10/2009 |
| WO | WO2015108091 A1 | 7/2015 |
| WO | WO2016103873 A1 | 6/2016 |
| WO | WO2018159093 A1 | 9/2018 |

OTHER PUBLICATIONS

Supplemental International Search Report and Written Opinion, PCT/CN2014/094892, dated Feb. 13, 2017.

All Office Actions, U.S. Appl. No. 15/632,447.

* cited by examiner

WEARABLE ARTICLE HAVING ELASTIC BELT

CROSS REFERENCE TO RELATED APPLICATIONS

This application is a continuation, under 35 USC 120, of Application No. PCT/CN2014/094892, filed on Dec. 25, 2014, which is herein incorporated by reference in its entirety.

FIELD OF THE INVENTION

The present invention relates to absorbent articles of small size having an elastic belt having specific dimensions.

BACKGROUND OF THE INVENTION

Pant-type absorbent articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. Belt-type pants are advantageous in that they have good breathability around the elastic belt, and in that they may be manufactured economically.

Compared to taped-type absorbent articles, pant-type absorbent articles are recently increasing popularity due to the convenience of applying a pant-type absorbent article on a child. When applying a taped-type article with comfortable fit on a child, the care-giver needs to pay close attention to the positioning of the article relative to the child's body and the stretching level applied in taping the ears to its landing zone. In contrast, pant-type articles have predefined waist opening and leg openings and thus allows the care-giver to apply the article on the child's body by simply inserting the child's legs in the leg opening and pulling the article up over the waist.

Small size pants are intended for use on infants having a body weight of less than 8 kg. Infants of this body size are typically less than 10 months old and, on average, sleep about 13-18 hours a day. For these infants, absorbent articles may be changed while they are sleeping, thus it is desirable that the small size pant may be applied onto infants with ease so that their sleep is not disturbed. Furthermore, the proportion of the lower torso and thighs of infants are different compared to older babies, and the legs of infants are usually in a curved position. Hence, simply downsizing larger sized pants does not provide a desirable small size pant for an infant.

Based on the foregoing, there is a need for providing a small size pant which can be applied with ease, has good fit on the wearer, and which can be made in a cost effective manner.

SUMMARY OF THE INVENTION

The present invention is directed to a wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other, and at least a portion of the elasticity of at least some of the elastic bodies are removed of its elasticity, the transverse width of the elastic body having the longest length removed of its elasticity defined as a maximum elastic cut window;

wherein the length of the article along the longitudinal axis is from 300 mm to 440 mm;

and the maximum elastic cut window is less than 100 mm.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Contracted state" refers to a state wherein the elastic body(ies) of the article is allowed to contract under an unused condition, and free from any stretching force. "Uncontracted state" refers to a state wherein the elastic body(ies) or the ring-like elastic belt of the article is stretched to the maximum dimension of the substrate supporting the elastic body(ies).

DETAILED DESCRIPTION OF THE INVENTION

Figure 1:
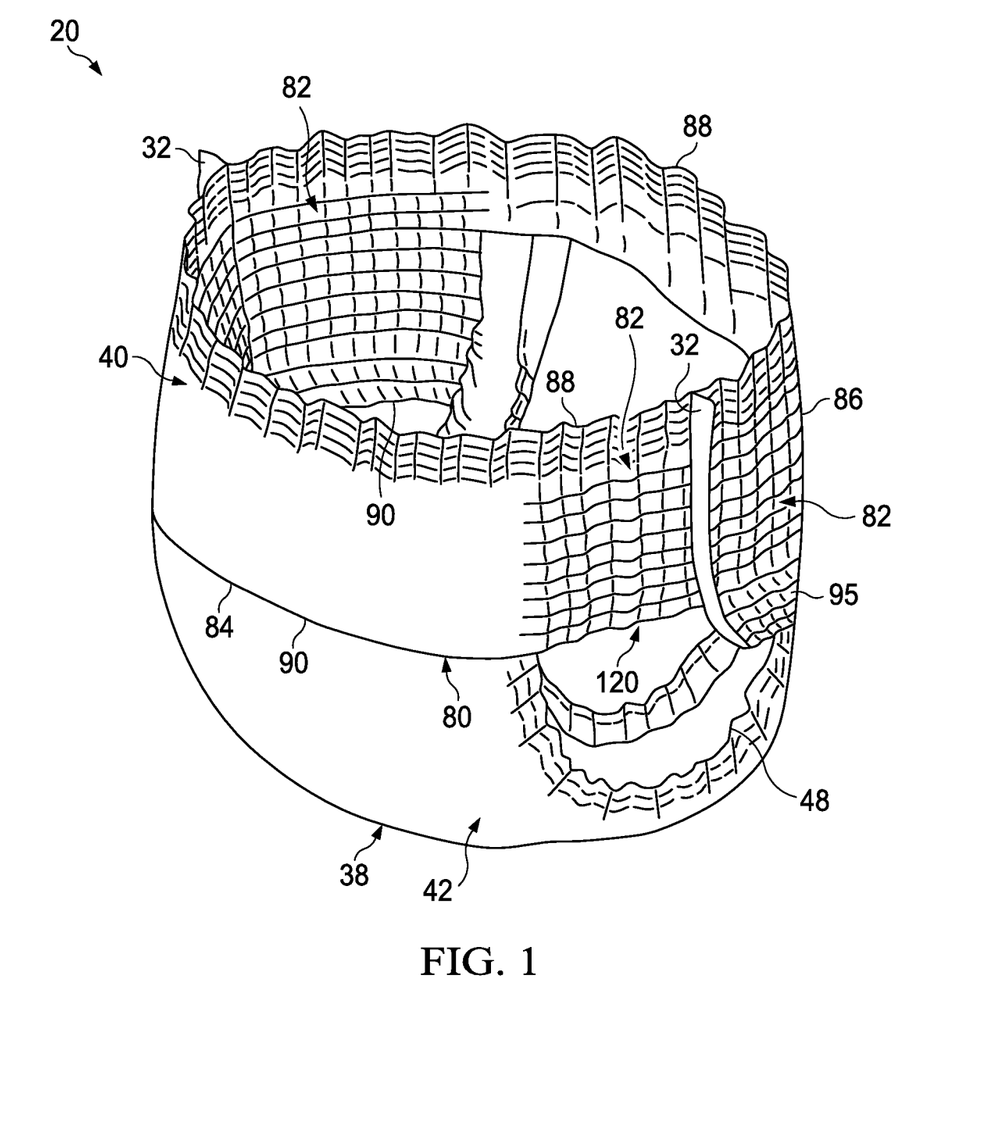
FIG. 1 is a perspective view of one embodiment of a wearable article of the present invention.
Figure 2:
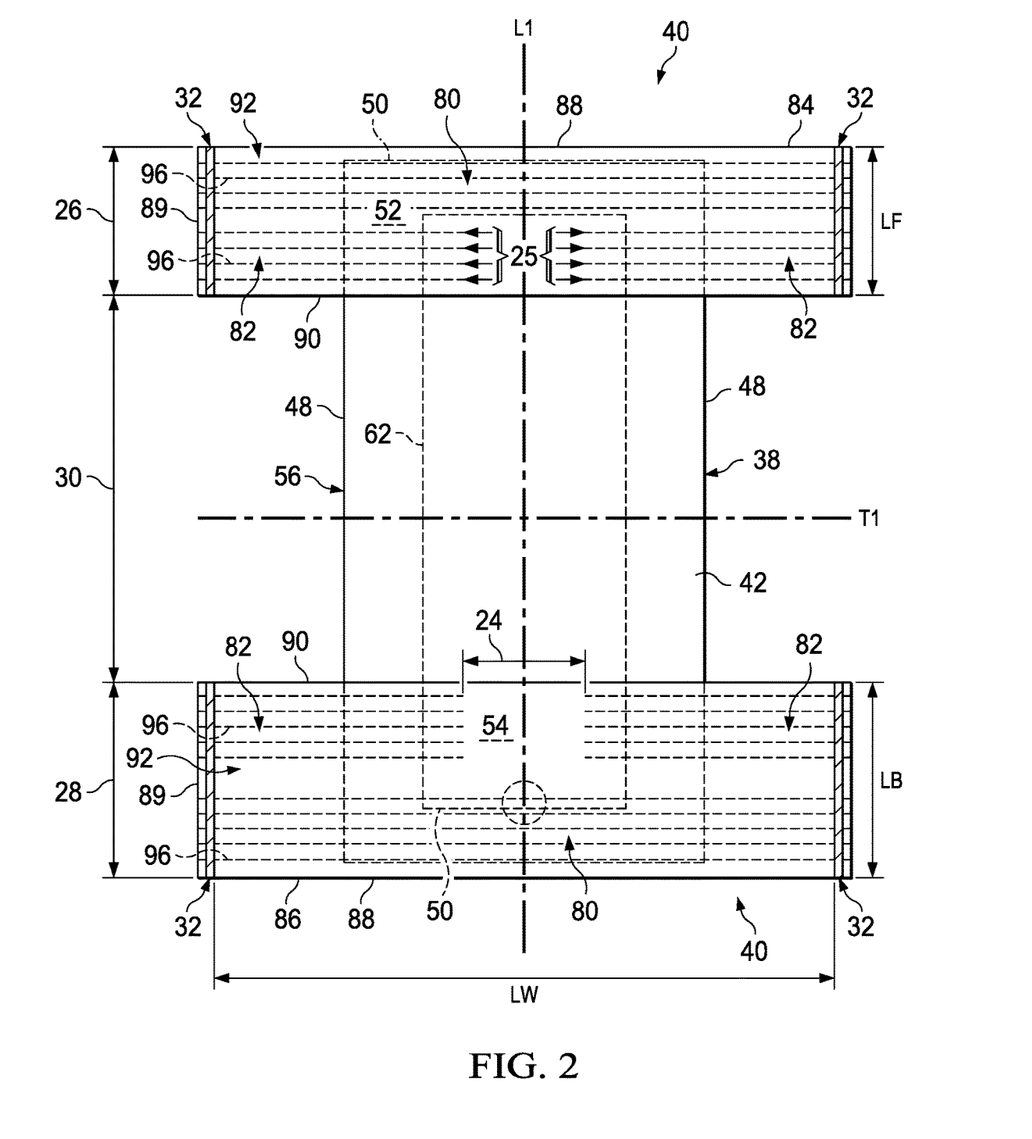
FIGS. 2-5 are schematic plan views of embodiments of a wearable article of the present invention in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap. The main body 38 may comprise a pair of leg elastics along the longitudinally extending side edges 118 each leg elastic having a leg elastic length Le which is the length of the leg elastic in contracted state between the proximal edges of the front belt and the back belt.

Referring to FIGS. 1 and 2, the ring-like elastic belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, the front belt 84 and back belt 86 may each comprise an inner sheet 94, an outer sheet 92, (hereinafter also collectively "belt sheets") and a plurality of elastic bodies 96 sandwiched therebetween and running in the transverse direction substantially parallel to each other, and configured to impart elasticity per each zone according to the relationship described below. (The inner sheet 94 is not shown.) Such an article may be economically made.

In one embodiment, the transverse width LW of the back belt 86 in the uncontracted condition may be the same as the transverse width of the front belt 84 of the same condition. In one embodiment, each of the proximal edges 90 and the distal edges 88 of the front belt 84 and the back belt 86 may be substantially parallel, as in FIG. 2.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90. In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in non-woven material having a basis weight of less than 25 gsm for sake of breathability perception and softness of the belt 40.

The tensile stress (N/m) of the front and back elastic belts 84, 86, respectively, may be profiled in order to provide the benefits of the present invention. The waist belt 40 exhibits elasticity due to the plurality of elastic bodies 96 running in the transverse direction, wherein the elastic bodies 96 adhered to the inner and outer sheets 92, 94 impart elasticity to the waist belt 40. Tensile stress of the waist belt 40 may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body 96. Each elastic body 96 disposed on the waist belt 40 may be disposed over the entire transverse width LW. Some elastic bodies 96 may be removed of its elasticity contributing to the elasticity of the waist belt 40 in the transverse center of the front and/or back belt 84, 86. When a portion of an elastic body is not contributing to the elasticity of the waist belt 40, the remainder of the intact elastic body capable of imparting elasticity to the waist belt 40 is defined as the "effective length of elasticity of an elastic body". An elastic body unadhered to the inner and outer sheets 92, 94 may be left dangling, thereby still exhibiting elasticity as an elastic body per se. However, so long as the elasticity is non-contributory to elasticity of the waist belt 40, such length or area is described herein as "non-elastic".

In the present invention, the elasticity of the elastic body 96 may be removed by the steps of:

(a) advancing the inner and outer sheets 92 94, in a machine direction;

(b) advancing and stretching the elastic body 96 in the machine direction;

(c) adhering the elastic body 96 between the inner and outer sheets 92, 94 wherein at least a certain portion of the elastic body is left unadhered, the unadhered portion being an elastic cut window 24; and (d) cutting the elastic body at the elastic cut window 24.

As such, the transverse width of the elastic cut window 24 defines the length for which the elasticity of the elastic body 96 is removed. The front or back belt 84, 86 may comprise a plurality of elastic bodies 96 having an elastic cut window 24. The accumulative elastic cut windows for a front belt 84 or a back belt 86 is herein defined as a set of elastic cut windows 25. The accumulative area wherein the set of elastic cut windows 25 exist may create a non-elastic region for the front or back belt 84, 86. There may exist a set of elastic cut windows 25 per one front belt 84 or per one back belt 86. For each set of elastic cut windows 25, the transverse width may be consistent to provide more or less a rectangular non-elastic region, or the transverse width of the elastic cut windows 24 may be varied. When the elastic cut windows 24 within a set of elastic cut windows 25 has a varied transverse width, the widest elastic cut window is defined as a maximum elastic cut window 24W.

The front and back belts of the present invention may have a maximum elastic cut window 24W of no more than 100 mm, or from 20 mm to 80 mm, and a transverse belt width LW of no less than 320 mm, or from 320 mm to 440 mm. In order to provide an elastic belt having such maximum elastic cut window 24W and belt width LW, the non-elastic region is provided relatively small in proportion, compared to larger size pants. Such configuration provides a bigger difference in waist opening circumference in the contracted state and the uncontracted state. Accordingly, the article of the present invention has an Initial Gauge Circumference and a Full Stretch Circumference according to the Whole Article Force Measurement described below, the Initial Gauge Circumference representing the elastic belt circumference in the contracted state before use, and the Full Stretch Circumference representing the elastic belt circumference in the stretched state during regular use conditions without excess efforts.

The articles of the present invention may have a Full Stretch Circumference of from 620 mm to 720 mm, or from 640 mm to 710 mm, and the ratio of the Full Stretch Circumference to the Initial Gauge Circumference may be at least 2.5.

Figure 7:
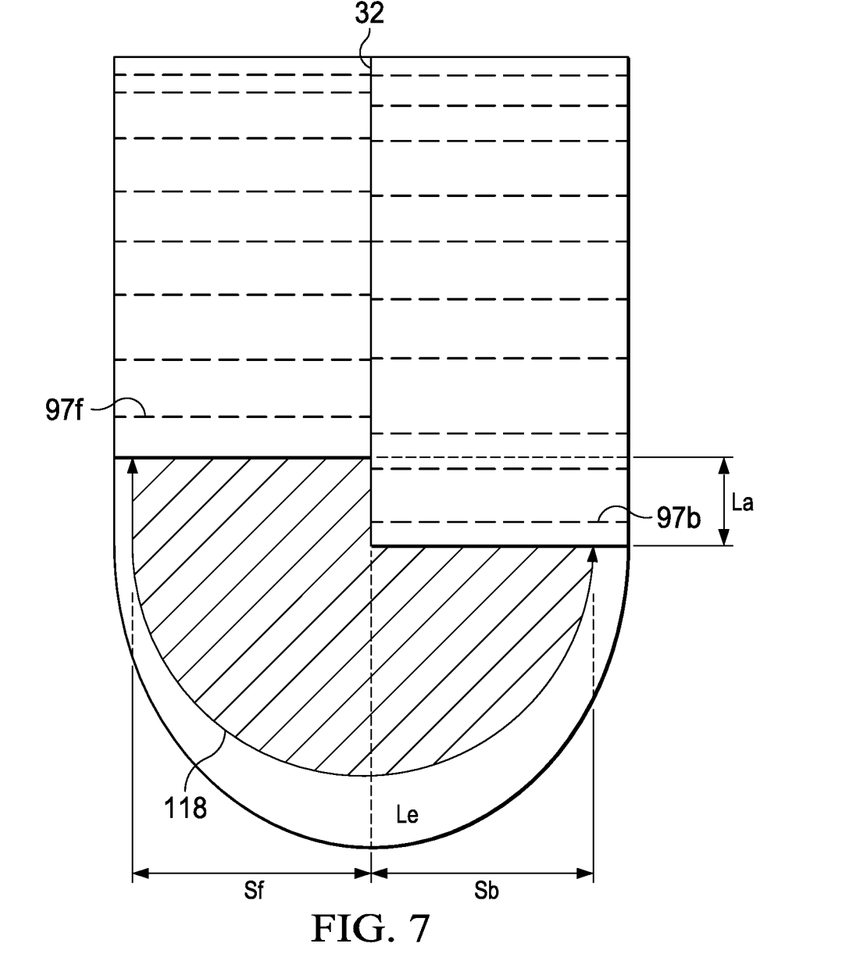
FIG. 7 is a schematic right side view of one embodiment of a wearable article of the present invention related to the "Leg Opening Length Measurement".

Referring to FIG. 7, the main body 38 may comprise a pair of outmost leg elastic bodies 118 along the longitudinally extending side edges, each outmost leg elastic body having a leg elastic length Le which is the length of the outmost leg elastic body in contracted state between the proximal edges of the front belt and the back belt. A plurality of elastic bodies may be disposed per side edge of the main body 38 for forming a gasketing cuff, however, only the outmost leg elastic body 118 disposed adjacent the side edge 48 is utilized for obtaining the leg elastic length Le. The front belt may have a front side panel elastic length Sf which is the length of the elastic body 97*f* disposed adjacent the proximal edge of the front belt 84 in contracted state between the seam 32 and the closest outmost leg elastic body 118. The back belt may have a back side panel elastic length Sb which is the length of the elastic body 97*b* disposed adjacent the proximal edge of the back belt 86 in contracted state between the seam and the closest outmost leg elastic body 118. The seam may have a longitudinal length difference La between the proximal edge of the front belt 84 and the proximal edge of the back belt 86. The leg opening may have a Leg Opening Length according to the Leg Opening Length Measurement described below. The article of the present invention may have a Leg Opening Length of from 150 mm to 300 mm, or from 160 mm to 285 mm.

For small size articles, the aforementioned dimensions related to Initial Gauge Circumference, Full Stretch Circumference, and Leg Opening Length may provide the desirable ease of application as well as waist and leg fit. Without intending to be bound by theory, it is believed that the dimension of Full Stretch Circumference and the ratio of the Full Stretch Circumference to the Initial Gauge Circumference as defined in the present invention provides a stretched waist opening which is wide enough to allow the care giver to pull the article through an infant's legs with ease, meanwhile, the waist opening in contracted state of the diaper will not be too big to cause sagging in use. Similarly, the dimension of the leg opening length as defined in the present invention provides the desirable leg fit to a wearer. The leg opening length in this range may also prevent leakage and gather marks.

In one embodiment, according to the Leg Opening Length Measurement, the Leg Elastic Length Le is no more than 75%, or from 55% to 70% of the Leg Opening Length. Such percentage of Leg Elastic Length Le to the Leg Opening Length may provide prevention of leakage.

Further, providing a larger Full Stretch Circumference enables making the article with a relatively wide transverse belt width LW. As such, the small size article of the present invention may be made by starting materials of the elastic belt 40 having the same belt width LW as those of larger sizes. For larger size articles, the elastic cut window and profile of elastic bodies may be changed. The capability of using starting materials having a common belt width LW for making articles of different sizes provides significant manufacturing efficiency from a capital investment and maintenance point of view. Moreover, despite such commonality, each article may be provided without compromise to performance such as fit and containment capability.

Referring to FIGS. 2-5, removal of elasticity from at least a portion of the area overlapping the front and/or back waist panel 52, 54 of at least one elastic body may be advantageous when the main body 38 comprises an absorbent core 62, in that elasticity in the front and/or back area may cause bunching of the absorbent core 62 and interfere with close fit of the main body 38 to the wearer. As described above, the article of the present invention may have a maximum elastic cut window 24W of less than 100 mm, or less than 95 mm, or less than 90 mm, or less than 80 mm, providing a non-elastic region which is relatively small in proportion, compared to larger size pants. Due to such narrower non elastic region, there may be elasticity remaining in areas overlapping the transverse side edges of the absorbent core 62. In other words, the maximum elastic cut window 24W may be 10 mm to 90 mm shorter than the transverse width of the absorbent core 62. Such configuration may be advantageous for small size pants in that this helps close fit of the main body and optional absorbent core to the wearer's body, while also fitting the wearer's smaller hip circumference. This is believed to help prevent gather marks while also preventing urine leakage.

Referring again to FIGS. 2, 3, and 5, the present article may have a single elastic body or an array of 2 elastic bodies on at least one of the front belt 84 and the back belt 86 which is disposed overlapping the absorbent core 62 and adjacent the distal edge of the absorbent core 62, and having elasticity over the entire transverse width of the at front or back belt 84, 86, the overlapping elastic body emphasized by circles in each Figure. Such overlapping elastic body may be a single elastic body as in FIGS. 2-3, or one array made of 2 elastic bodies disposed in the interval in the longitudinal direction of no more than 4 mm, as in FIG. 5. Without being bound by theory, by disposing the elastic bodies in such close proximity to each other, the array exhibits a behavior as if it were one elastic body with a certain width, and provides various benefits. For example, the array provides more or less the combined tensile force of the elastic bodies in the array, such that each elastic body may be disposed at a much lower tensile force. The elastic body for which overlaps the absorbent core may have a density of 470-1100 dtex, and disposed at an elongation of from 150% to 300%.

Figure 3:
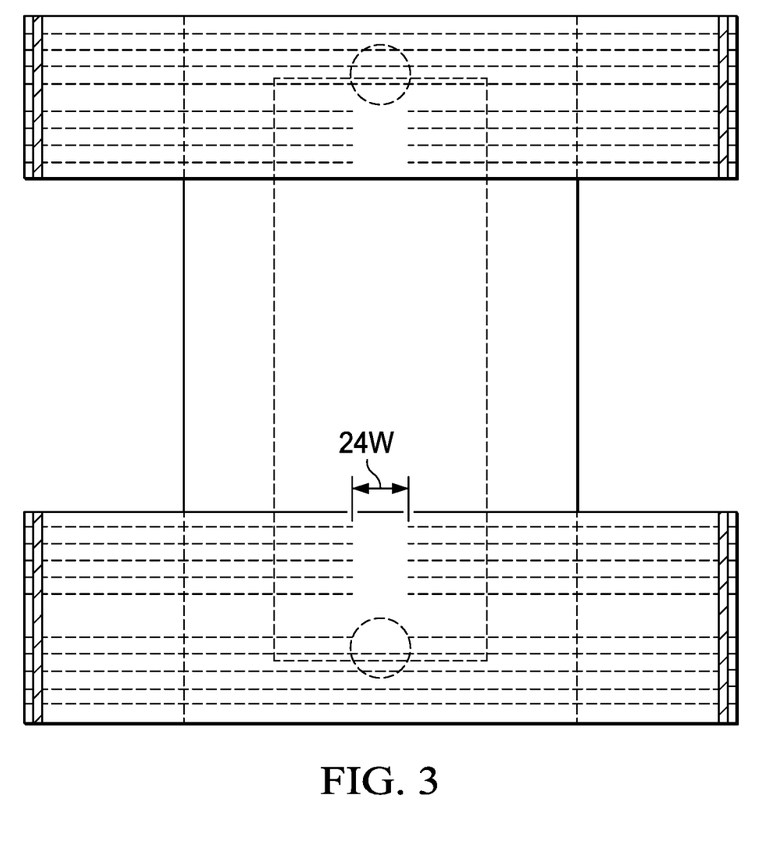
Figure 4:
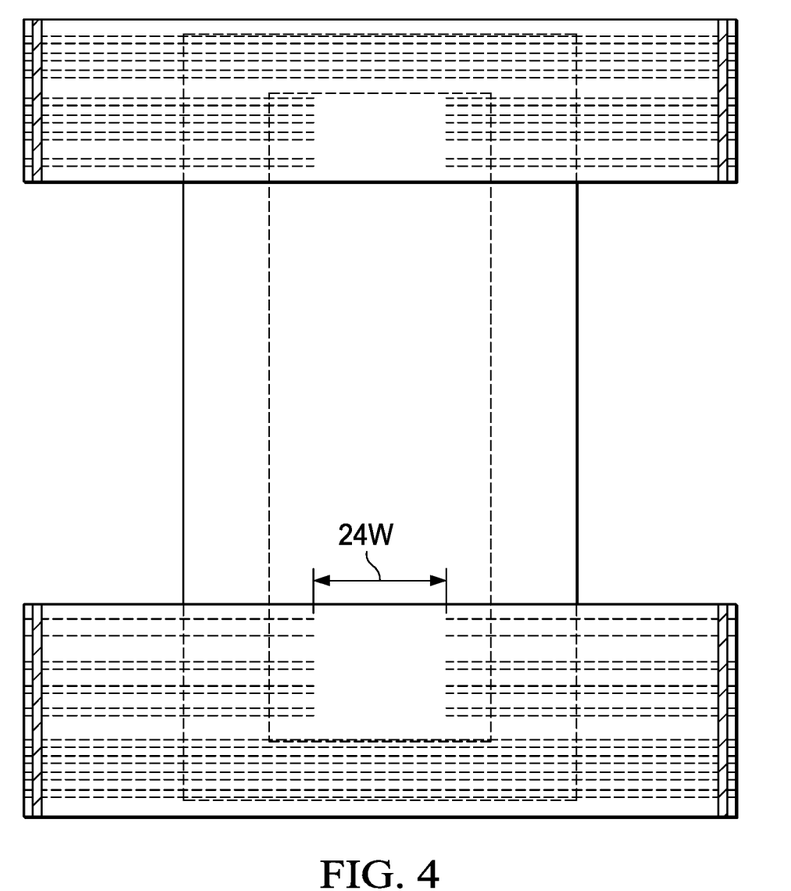
Figure 5:
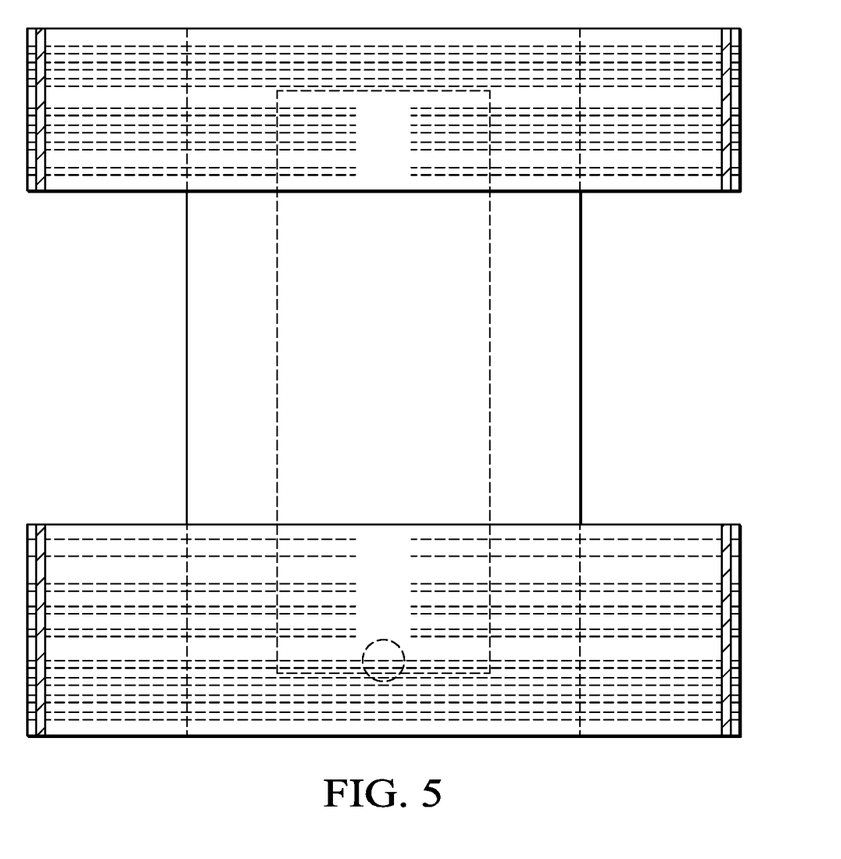

Without being bound by theory, the overlapping elastic body prevents creating a gap between the area where the absorbent core overlaps and not, by providing a gradation of tensile stress between the area where the elastic bodies are disposed along the entire circumference, and the area where some elastic bodies 96 do not exhibit elasticity. By having just one or one array of an overlapping elastic body, the absorbent core 62 may be fit closer to the wearer, while also avoiding bunching up of the majority of the area of the absorbent core 62 overlapping with the waist belt 40. Further, by preventing creation of such a gap which may obviate the existence of the absorbent core 62, the absorbent article may have a garment like appearance.

The elastic profiling described herein may be utilized for economically making an article of from 300 mm to 440 mm, or from 350 mm to 440 mm in the longitudinal axis by using a total of no more than 40, or from 15 to 40 elastic bodies for the elastic belt 40 per article. In the embodiments of FIGS. 3 and 5, the longitudinal ends of the main body 38 matches with the distal edges of the front and back belts 84, 86.

The article of the present invention may have a Waist Circumference Force provided by the elastic bodies 96 disposed on the waist belt 40 of no more than 10N, or no more than 8N, according to the Whole Article Force Measurement as described herein below. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

The obtained wearable article of the present invention may provide fit, ease of application, prevention of leakage and gather marking around the leg opening. The obtained wearable article of the present invention may be made in an economical manner.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 6:
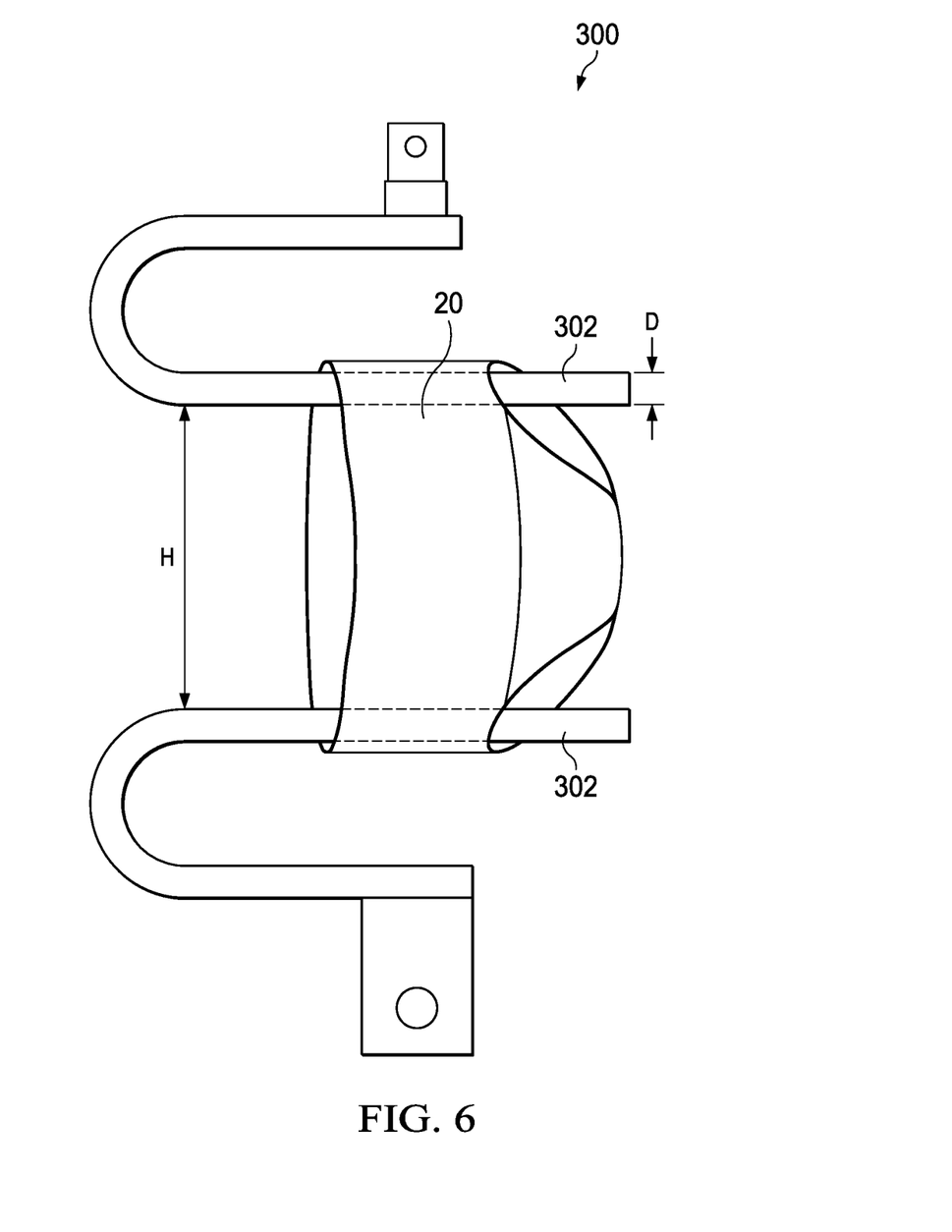
FIG. 6 is a schematic view of an example of a hanger-type sample holding fixture according to the "Whole Article Force Measurement".

The tensile tester is fitted with hanger-type sample holding fixtures 300 as shown in FIG. 6. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the initial gauge circumference at the same speed. The maximum circumference at 19.6N and the force at 70% stretch circumference during the extension segment of the test are recorded.

$$\text{Circumference (mm)} = 2 \times (H + D + \pi D/2)$$

The maximum circumference at 19.6N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

Leg Opening Length Measurement

The measurement is for obtaining the leg opening length of an article. Care is taken not to tear the side seam 32. Referring to FIG. 7, the length of the outmost leg elastic body 118 in contracted state between the proximal edges of the front belt and the back belt is measured and defined as Leg Elastic Length Le. It is measured by using conventional flexible ruler which typically used for body measurement as follows. 1) Attach the zero point of the flexible ruler at the body facing side of the point where the proximal edge of the front belt and the outmost leg elastic 118 are crossed. 2) Make the flexible ruler follow body facing side of the outmost leg elastic 118 towards the proximal edge of the back belt 86 without stretching the outmost leg elastic 118. (Without stretch means maintaining leg elastic stretch no more than 10%.) 3) Read the flexible ruler in nearest 1 mm at the point where the proximal edge of the back belt and the outmost elastic are crossed.

The length of the elastic body 97f disposed adjacent the proximal edge of the front belt 84 in contracted state between the seam 32 and the closest outmost leg elastic body 118 is measured and defined as the Front Side Panel Elastic Length Sf. The length of the elastic body 97b disposed adjacent the proximal edge of the back belt 86 in contracted state between the seam 32 and the closest outmost leg elastic body 118 is measured and defined as the Back Side Panel Elastic Length Sb. The length along the seam between the proximal edge of the front belt 84 and the proximal edge of the back belt 86 is measured and defined as the Seam Length Difference La. These measurements can be done by using conventional stainless steel ruler as follows. 1) Insert a hand to the leg opening to flatten the belt side panel on the palm. 2) Measure the distances in nearest 1 mm between the points.

The Leg Opening Length LO is obtained by the following formula.

$$LO = Le + Sf + \sqrt{Sb^2 + La^2}$$

EXAMPLES

Examples 1 and 2

A wearable article of the present invention having an elastic profiling according to FIGS. 2, 3, and the table below having a belt width LW of 355 mm, a front belt length LF of 85 mm, and a back belt length LB of 111 mm.

| Example | 1 (FIG. 2) | 2 (FIG. 3) |
|---|---|---|
| Size | NB (1) | S (2) |
| Front belt elastics distal side (dtex/prestretch %/#of elastics) | 940 dtex/275%/4 | 940 dtex/232%/4 |
| Front belt elastics proximal side with elastic cut window (dtex/prestretch %/#of elastics) | 680 dtex/275%/4 | 680 dtex/275%/4 |

-continued

| Example | 1 (FIG. 2) | 2 (FIG. 3) |
| --- | --- | --- |
| Back belt elastics distal side (dtex/prestretch %/#of elastics) | 940 dtex/275%/2 1100 dtex/275%/2 | 940 dtex/232%/2 1100 dtex/230%/2 |
| Back belt elastics proximal side with elastic cut window (dtex/prestretch %/#of elastics) | 680 dtex/275%/3 | 680 dtex/275%/3 |
| Back belt elastics buttock cover with elastic cut window (dtex/prestretch %/#of elastics) | 680 dtex/232%/1 1100 dtex/232%/1 | 680 dtex/232%/1 1100 dtex/232%/1 |
| Elastic cut window | 30 mm | 70 mm |
| Design weight range | 2~5 kg | 4~8 kg |
| Initial Gauge Circumference (IGC) | 209 mm | 238 mm |
| Full Stretch Circumference (FSC) | 681 mm | 681 mm |
| Ratio FSC/IGC | 3.3 | 2.9 |
| Leg Elastic Length (LEL) | 95 mm | 120 mm |
| Leg Opening Length (LO) | 166 mm | 193 mm |
| LEL/LO (%) | 57% | 62% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings,
   wherein each of the front belt and back belt are formed by an inner sheet, an outer sheet, and a plurality of elastic bodies sandwiched therebetween and running in the transverse direction substantially parallel to each other, and at least a portion of the elasticity of at least some of the elastic bodies are removed of its elasticity, a transverse width of the elastic body having a longest length removed of its elasticity defined as a maximum elastic cut window;
   wherein a length of the article along the longitudinal axis is from 300 mm to 440 mm; and
   the maximum elastic cut window is less than 100 mm.

2. The article of claim 1 wherein the front belt and the back belt have a same transverse length, and the transverse length is no less than 320 mm.

3. The article of claim 2 having an Initial Gauge Circumference and a Full Stretch Circumference according to a Whole Article Force Measurement disclosed herein, wherein the Full Stretch Circumference is from 620 mm to 720 mm, and the ratio of the Full Stretch Circumference to the Initial Gauge Circumference is no less than 2.5.

4. The article of claim 1 wherein each of proximal edges and distal edges of the front belt and the back belt are substantially parallel, the longitudinal length of the back belt being longer than that of the front belt, wherein the distal edge of the front belt is aligned with the distal edge of the back belt, and a proximal edge of the front belt is not aligned with a proximal edge of the back belt.

5. The article of claim 4 wherein the main body comprises a pair of outmost leg elastic bodies along the longitudinally extending side edges, wherein a Leg Opening Length according to a Leg Opening Length Measurement disclosed herein is from 150 mm to 300 mm.

6. The article of claim 5, wherein a Leg Elastic Length is no more than 75% of the Leg Opening Length according to a Leg Opening Length Measurement disclosed herein.

7. The article of claim 1 wherein the main body comprises an absorbent core, the absorbent core overlapping an area of the front belt and the back belt wherein the elastic bodies are removed of elasticity, wherein the maximum elastic cut window is at least 10 mm shorter than a transverse width of the absorbent core.

8. The article of claim 1 wherein there is a single array of elastic body on at least one of the front belt and the back belt which is disposed overlapping an absorbent core and adjacent a distal edge of the absorbent core, and having elasticity over an entire transverse width of the at front or back belt.

9. The article of claim 8 wherein the single array is a single elastic body or an array of 2 elastic bodies disposed in an interval in the longitudinal direction of no more than 4 mm, wherein the elastic body for forming the single array has a density of 470-1100 dtex, and is disposed at an elongation of from 150% to 300%.

10. The article of claim 1 wherein the elastic belt is disposed of a total of no more than 40 elastic bodies.

11. The article of claim 1 wherein a Waist Circumference Force according to a Whole Article Force Measurement disclosed herein is no more than 10N.

12. The article of claim 1 wherein a Waist Circumference Force according to a Whole Article Force Measurement disclosed herein is no more than 8N.

13. The article of claim 4 wherein the main body comprises a pair of outmost leg elastic bodies along the longitudinally extending side edges, wherein a Leg Opening Length according to a Leg Opening Length Measurement disclosed herein is from 160 mm to 285 mm.

14. The article of claim 1 wherein the seam has a longitudinal length difference "La" between a proximal edge of the front belt and a proximal edge of the back belt.

15. The article of claim 1 wherein the main body comprises an absorbent core, the absorbent core overlapping an area of the front belt and the back belt wherein the elastic bodies are removed of elasticity.

16. The article of claim 1 wherein there is a single array of elastic body on at least one of the front belt and the back belt which is disposed overlapping an absorbent core and adjacent a distal edge of the absorbent core.

17. The article of claim 8 wherein the single array is a single elastic body or an array of 2 elastic bodies disposed in an interval in the longitudinal direction of no more than 4 mm.

18. The article of claim 2 having an Initial Gauge Circumference and a Full Stretch Circumference according to a Whole Article Force Measurement disclosed herein.

* * * * *